United States Patent [19]

Barchas et al.

[11] 4,134,910

[45] Jan. 16, 1979

[54] RECOVERY OF ISOPHTHALONITRILE

[75] Inventors: Richard K. Barchas, Upper Montclair; Abraham P. Gelbein, Plainfield; William J. Santore, Bloomfield, all of N.J.

[73] Assignee: The Lummus Company, Bloomfield, N.J.

[21] Appl. No.: 797,810

[22] Filed: May 17, 1977

[51] Int. Cl.² ............................................. C07C 121/54
[52] U.S. Cl. ............................. 260/465 H; 260/465 C
[58] Field of Search ........................ 260/465 C, 465 H

[56] References Cited

U.S. PATENT DOCUMENTS 3,732,275  5/1973  Platz et al. ........................ 260/465 C

*Primary Examiner*—Dolph H. Torrence
*Attorney, Agent, or Firm*—Marn & Jangarathis

[57] ABSTRACT

Isophthalonitrile (IPN) is recovered from an isophthalonitrile production reaction effluent, which contains water vapor, by direct contact quenching of the effluent with an organic quench liquid to cool the effluent to a temperature at which essentially all of the isophthalonitrile is condensed as a solution in the organic quench liquid, without condensation of water vapor. In this manner, isophthalonitrile is recovered from the effluent and separated from water vapor, thereby preventing the liquid phase hydrolysis of IPN which occurred in prior art procedures.

7 Claims, 1 Drawing Figure

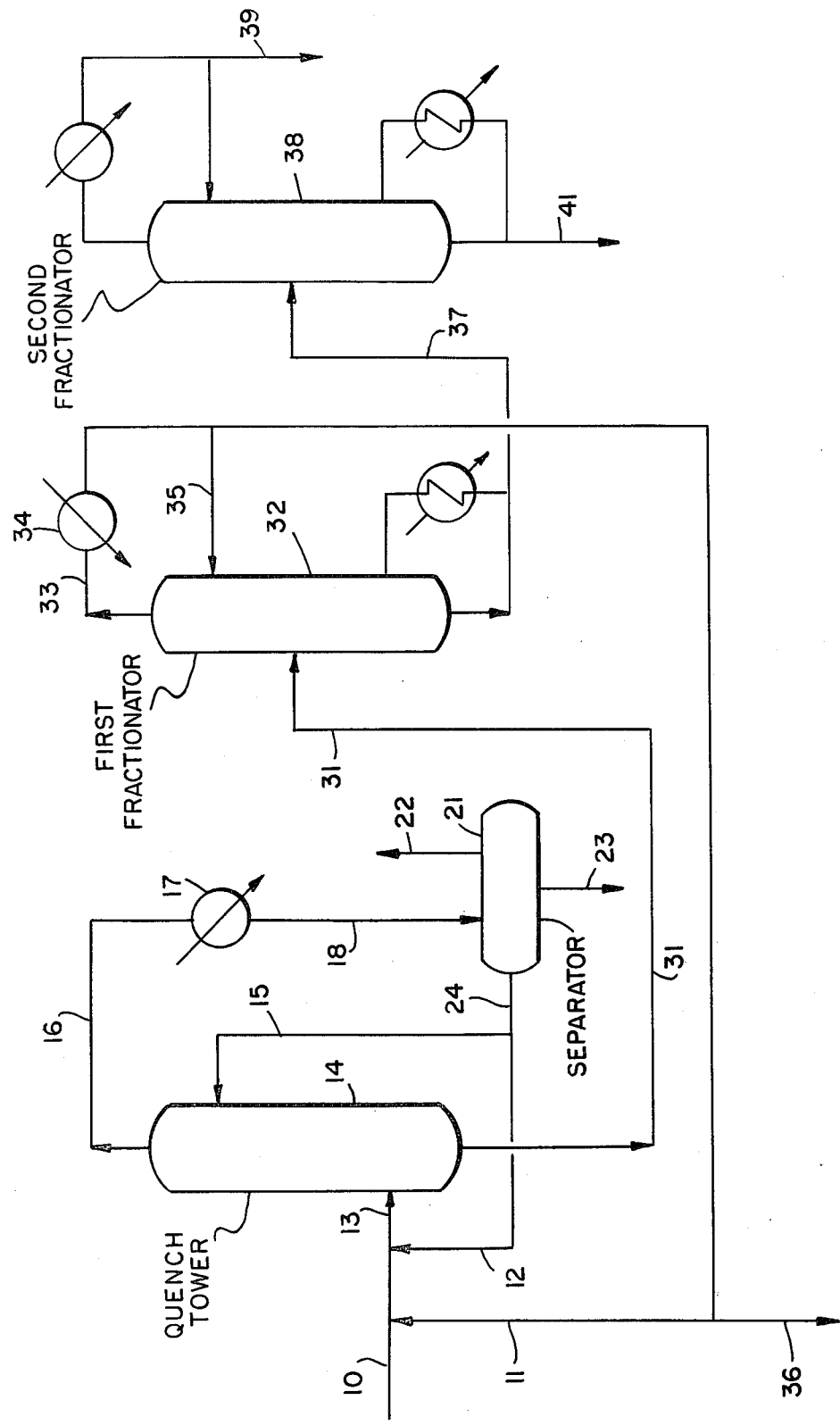

RECOVERY OF ISOPHTHALONITRILE

This invention relates to the recovery of isophthalonitrile (IPN) and more particularly, to a process for recovering IPN from an IPN production reaction effluent.

In the production of IPN from m-xylene, IPN is generally recovered from the effluent by direct contact quenching with water to produce solid or liquid IPN, as disclosed, for example, in U.S. Pat. No. 3,472,891 or U.S. Pat. No. 3,801,620.

Applicant has found, however, that the use of such an aqueous quench may lead to the hydrolysis of a portion of the recovered IPN, and as a result, there is a need for an improvement in such procedures for recovering IPN from an IPN production reaction effluent.

Although U.S. Pat. No. 3,732,275 discloses the use of an organic quench, the overall quenching procedure does not avoid nitrile loss by hydrolysis in that the procedure does not provide for complete separation of nitrile product and water.

The object of this invention is to provide for improved recovery of isophthalonitrile.

Another object of the present invention is to effect recovery of isophthalonitrile while preventing hydrolysis of the nitrile product.

These and other objects of the present invention should be more readily apparent from reading the following detailed description thereof.

In accordance with the present invention, an isophthalonitrile production reaction effluent, including IPN, unconverted m-xylene, ammonia, m-toluonitrile, benzonitrile, m-cyanobenzamide, carbon monoxide, carbon dioxide, nitrogen, hydrogen cyanide and water vapor, is contacted with an organic quench liquid, preferably one which is indigenous to the process, to cool the effluent to a temperature at which essentially all of the IPN is condensed from the effluent as a solution in the quench liquid, without condensation of water vapor to thereby effect an essentially complete separation of IPN and water to thereby prevent hydrolysis of IPN in the recovery operation.

More particularly, the organic quench liquid is employed at a temperature and in a quantity whereby the effluent is cooled to a temperature which is above the dew point of the water in the effluent, but sufficiently close to the dew point of water, whereby essentially all of the IPN Is separated from the effluent as a solution in the organic quench liquid. In general, the quench liquid is employed at a temperature from 50° F to 150° F and preferably from 80° F to 120° F. The effluent, prior to contact with the organic quench liquid, is at a temperature of from 350° F to 850° F, and subsequent to the quenching, the effluent is at a temperature above the water dew point, generally at a temperature of from 170° F to 240° F, preferably from 190° F to 220° F. The effluent is generally quenched to a temperature which is from 20° F to 70° F, preferably from 30° F to 50° F, above the water dew point. The quenching is effected at a pressure of from 0 psig to 50 psig, with the quench liquid being employed in a quench liquid to effluent weight ratio of from 0.5:1 to 1.5:1, and preferably from 0.8:1 to 1.2:1. Subsequent to the quenching, the uncondensed portion of the gaseous effluent contains essentially no IPN, and the condensed solution of IPN in the quench liquid is free of water.

The organic quench liquid is preferably one which is indigenous to the process and, accordingly, the preferred quench liquid is comprised of one or more of m-xylene, m-toluonitrile, or benzonitrile. The IPN is subsequently recovered from the solution as reaction product; e.g., by fractional distillation, crystallization, etc.

The IPN production reaction effluent is produced by any one of a wide variety of procedures which involve reaction between m-xylene and ammonia, and in the presence of a suitable catalyst. Thus, for example, such a procedure is described in U.S. Pat. No. 3,925,447. In general, such an effluent has a water vapor partial pressure in the order of from 3 to 8 psia.

The present invention will be further described with respect to an embodiment thereof illustrated in the accompanying drawing, wherein:

The drawing is a simplified schematic flow diagram of an embodiment of the present invention.

Referring now to the drawing, an IPN production reaction effluent, including IPN, unconverted m-xylene, ammonia, m-toluonitrile, benzonitrile, m-cyanobenzamide, carbon monoxide, carbon dioxide, nitrogen, hydrogen cyanide and water vapor, in line 10, is directly contacted with an organic quench liquid in line 11 and in line 12, obtained as hereinafter described, to effect cooling of the effluent to a temperature at which essentially all of the IPN is condensed from the effluent as a solution in the quench liquid, with such temperature being a temperature above the dew point of water in the effluent, whereby the condensate is free of water. The combined stream in line 13 is introduced into a quench tower 14.

The uncondensed portion of the effluent is further contacted in the top portion of quench tower 14 with additional quench liquid introduced through line 15 in order to remove from the gaseous portion any remaining IPN.

The uncondensed portion of the effluent is withdrawn from tower 14 through line 16, cooled in cooler 17 and the cooled stream in line 18 introduced into a separator 21. In separator 21, an organic and aqueous phase are separated from a remaining gaseous stream, which is withdrawn from separator 21 through line 22 for recycle to the IPN production reactor. The vapor stream in line 22 includes uncondensed m-xylene, benzonitrile, m-toluonitrile, ammonia, carbon monoxide, carbon dioxide, nitrogen and water vapor.

In separator 21, an aqueous phase is separated from an organic phase with the aqueous phase being withdrawn through line 23.

An organic phase, including m-xylene, m-toluonitrile and benzonitrile is withdrawn from separator 21 through line 24, and employed as quench liquid in lines 12 and 15.

A solution of IPN in the organic quench liquid, which is free of water, is withdrawn from quench tower 14 through line 31 and introduced into a fractional distillation tower, generally indicated as 32, to separate benzonitrile, m-xylene and m-toluonitrile from IPN and heavier components.

An overhead of benzonitrile, m-xylene and m-toluonitrile is withdrawn from fractionator 32 through line 33 and passed through condenser 34 to effect condensation of the overhead and produce a liquid which is at a temperature suitable for the quenching operation. It is to be understood, however, that cooling could be effected other than as particularly described.

The first portion of the condensed overhead is employed in line 35 as reflux to the fractionator 32. The second portion of the condensed overhead is employed as the quench liquid in line 11, and a further portion thereof in line 36 is recycled to the IPN production reactor.

A bottoms of IPN and heavier components is withdrawn from fractionator 32 through line 37 and introduced into a second fractionator 38 wherein IPN is separated from the heavier components. IPN is recovered from fractionator 38 as overhead through line 39 and the heavier components are recovered as a bottoms through line 41.

The present invention will be further described with respect to the following example; however, the scope of the invention is not to be limited thereby:

EXAMPLE

| Stream Number Flow lbs/hr. | 10 | 16 | 22 | 24 | 23 | 11 | 31 | 39 | 36 | 41 |
|---|---|---|---|---|---|---|---|---|---|---|
| M-Xylene | 2820 | 11150 | 1370 | 9780 | | 3380 | 4830 | | 1450 | |
| Benzonitrile | 150 | 130 | 6 | 124 | | 336 | 480 | | 144 | |
| M-Toluonitrile | 1520 | 190 | 4 | 186 | | 3544 | 5060 | | 1516 | |
| Isophthalonitrile | 1870 | | | | | 15 | 1885 | 1900 | 11 | 5 |
| M-Cyanobenzamide | 70 | | | | | | 70 | | | |
| $NH_4CN$ | | | | | 7 | | | | | |
| $NH_3$ | 5270 | 5270 | 4480 | | 790 | | | | | |
| $CO_2$ | 440 | 440 | 80 | | 360 | | | | | |
| CO | 410 | 410 | 410 | | | | | | | |
| $N_2$ | 1450 | 1450 | 1450 | | | | | | | |
| $H_2O$ | 3190 | 3190 | 530 | | 2660 | | | | | |
| HCN | 5 | 5 | | | | | | | | |
| Heavy Ends | | | | | | | | | 34 | 24 |
| Totals | 17195 | 22235 | 8330 | 10090 | 3817 | 7275 | 12325 | 1900 | 3121 | 29 |
| Temp. (° F) | 385° F | 195° F | 120° F | 120° F | 120° F | 120° F | 220° F | 525° F | 120° F | 600° F |
| Pressure (psig) | 6 | 5 | 2 | 2 | 2 | — | 6 | 1 | — | 3 |

The present invention is particularly advantageous in that it is possible to recover IPN from the reaction effluent, while simultaneously separating IPN from water, whereby IPN is not contacted in the liquid phase, with water, thereby preventing loss of valuable product which heretofore occurred by hydrolysis of the IPN.

Numerous modifications and variations of the present invention are possible within the above teachings and, therefore, within the scope of the appended claims, the invention may be practiced otherwise than as particularly described.

What is claimed is:

1. A process for separating isophthalonitrile from a gaseous isophthalonitrile production reaction effluent including isophthalonitrile and water vapor, comprising:
   direct quench cooling of the gaseous isophthalonitrile production reaction effluent with an organic quench liquid in which isophthalonitrile is soluble to effect cooling of the effluent to a temperature above the dew point of water in the effluent and at which essentially all of the isophthalonitrile is condensed from the effluent as a solution in the quench liquid and recovering from said direct quench cooling a gas containing water vapor which is essentially free of isophthalonitrile and a liquid solution of the isophthalonitrile in the quench liquid which is free of water.

2. The process of claim 1 wherein the quench liquid is employed at a temperature of from about 50° F to about 150° F.

3. The process of claim 2 wherein the effluent is quench cooled to a temperature of from about 170° F to about 240° F to effect said condensation of isophthalonitrile as a solution in said quench liquid.

4. The process of claim 3 wherein the quench effluent is at a temperature of from about 20° F to about 70° F above the dew point of water in the effluent.

5. The process of claim 4 wherein the organic quench liquid is comprised of m-xylene, m-toluonitrile, and benzonitrile.

6. The process of claim 5 wherein the reaction effluent also includes m-xylene, m-toluonitrile and benzontrile, a portion of which is also condensed, and further comprising separating a mixture of m-xylene, m-toluonitrile and benzonitrile from isophthalonitrile and employing a portion of said mixture as the quench liquid.

7. A process for separating isophthalonitrile from a gaseous isophthalonitrile production reaction effluent including isophthalonitrile, water vapor, m-xylene, m-tolunitrile, benzonitrile, and ammonia, comprising:
   direct quench cooling of the gaseous isophthalonitrile production reaction effluent with an organic quench liquid comprised of m-xylene, m-tolunitrile and benzonitrile, said quench liquid being at a temperature of from about 50° F to about 150° F to effect cooling of the effluent to a temperature of from about 20° F to about 70° F above the dew point of water in the effluent and at which essentially all of the isophthalonitrile is condensed from the effluent as a solution in the quench liquid, said effluent being cooled to a temperature of from about 170° F to about 240° F;
   recovering from said quench cooling a liquid solution of isophthalonitrile in the quench liquid;
   recovering from said quenching a gas containing water vapor, ammonia, uncondensed m-xylene, benzonitrile and m-tolunitrile which is essentially free of isophthalonitrile;
   cooling said gas to effect condensation of water vapor, said cooling condensing a portion of the m-xylene, m-tolunitrile and benzonitrile;
   separating isophthalonitrile from said quench liquid; and,
   recycling said quench liquid and m-xylene, m-tolunitrile and benzonitrile condensed from said cooling as quench liquid in said direct quench cooling.

* * * * *